(12) United States Patent
Rosing et al.

(10) Patent No.: US 8,030,372 B2
(45) Date of Patent: Oct. 4, 2011

(54) ANTIMICROBIAL COMPOSITIONS AND PRODUCTS

(75) Inventors: Howard S Rosing, Naples, FL (US); Yu-Te Lin, Taipei (TW); Chieh-Fu Huang, Dongguan (TW); Ronald I Pass, Naples, FL (US)

(73) Assignee: Global Biochemical Development, LLC, Naples, FL (US)

( * ) Notice: Subject to any disclaimer, the term of this patent is extended or adjusted under 35 U.S.C. 154(b) by 0 days.

(21) Appl. No.: 12/553,513

(22) Filed: Sep. 3, 2009

(65) Prior Publication Data

US 2011/0052651 A1    Mar. 3, 2011

(51) Int. Cl.
*C09D 5/16* (2006.01)
*D06M 13/224* (2006.01)
*C09K 15/16* (2006.01)
*C09K 15/22* (2006.01)

(52) U.S. Cl. ...... 523/122; 252/8.81; 252/8.84; 252/401; 252/403

(58) Field of Classification Search .................. 523/122; 252/8.81, 8.84, 401, 403
See application file for complete search history.

(56) References Cited

U.S. PATENT DOCUMENTS

| 5,882,357 A | 3/1999 | Sun |
| 2008/0102217 A1 | 5/2008 | Lin |

OTHER PUBLICATIONS

Montazer, M. et al., "Simultaneous X-Linking and Antimicrobial Finishing of Cotton Fabric", Journal of Applied Polymer Science, 2007, vol. 103, pp. 178-185. See p. 179; Experimental (fabric treatment); tables I-IV.
International Search Report and Written Opinion, mailing date of Sep. 14, 2010.

*Primary Examiner* — Kriellion A Sanders
(74) *Attorney, Agent, or Firm* — Thomas, Kayden, Horstemeyer, & Risley, LLP

(57) ABSTRACT

The present disclosure provides antimicrobial compositions for use in textiles, as well as methods of preparing these compositions and treating textiles with these compositions.

16 Claims, No Drawings

ANTIMICROBIAL COMPOSITIONS AND PRODUCTS

BACKGROUND

There are many reasons for wanting to incorporate antimicrobial agents into textiles. For instance, antimicrobial activity may enhance the durability of textiles by inhibiting the growth of bacteria and fungi that live in textiles and cause damage to their components. Textiles with antimicrobial activity also prevent the creation of odors by preventing or reducing microbes from feeding on the organic materials in the textile. Additionally, antimicrobial treated textiles may kill pathogenic microbes thereby protecting the wearer from exposure to disease agents.

Other uses of antimicrobial treated textiles include wound care. For example, a medical bandage that has been treated with antimicrobial agents offers the wound a favorable environment for healing and further prevents bacterial organisms from growing at the site. Furthermore, antimicrobial cleaning cloths may prevent disease-causing microorganisms from surviving or even proliferating in the internal crevices of the textile when the cloth soaks up contaminated fluid.

Antimicrobial bedding linens offer an enhanced level of hygiene and security in hospital or hotel rooms. Their use may limit the transmission of bacterial disease in hospitals and lower the rates at which hospitalized patients acquire nosocomial infections, which have been increasing in frequency in recent years.

While textiles possessing antimicrobial characteristics have been introduced in recent years, most of these textiles are prepared by adding antimicrobial agents to the textile. Specifically, antimicrobial agents are impregnated into or coated onto the fibers of the textile. The antimicrobial agents are not, however, permanently bound to the textile fibers and are thus prone to leaching, such that these agents are absorbed by human skin. In addition to leaching, the antimicrobial agents are not able to withstand numerous washings, so that the antimicrobial effect may not last long. While certain N-halamine treated textiles are known to be regenerable after exhaustion by the treated textiles, use of chlorine bleach is necessary to regenerate antimicrobial activity.

Thus, there is a need to overcome the aforementioned disadvantages. Current antimicrobial treatment of textile leaves a need for a means of providing various textiles with minimal leaching, more permanent antimicrobial characteristics, and that does not require use of chlorine bleach for regenerable antimicrobial properties.

DETAILED DESCRIPTION

Although particular embodiments are described herein, those embodiments comprise mere examples of the disclosed inventions and are not intended to limit this disclosure. Terminology used herein serves the purpose of describing those embodiments, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Ratios, concentrations, amounts, and other numerical data can be expressed herein in a range format. Such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. For illustration purposes only, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. The term "about" or "approximately" can include an acceptable error for a particular value as determined by one of ordinary skill in the art of general chemistry, organic chemistry, polymer chemistry, materials science, which depends in part on how the value is measured or determined. In certain embodiments, "about" can mean one or more standard deviations.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of general chemistry, organic chemistry, polymer chemistry, materials science, and the like, which are within the skill of the art. Such techniques are explained fully in the literature.

Prior to describing the various embodiments, the following definitions are provided and should be used unless otherwise indicated.

I. Definitions

Unless otherwise defined, all technical and scientific terms used herein have the same meaning as commonly understood by one of ordinary skill in the art of general chemistry, organic chemistry, polymer chemistry, and materials science. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, "DMDMH", or "DMDM hydantoin" refers to 1,3-dimethylol-5,5-dimethylhydantoin,

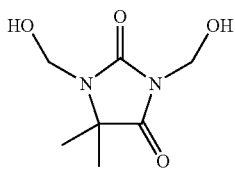

[i.e., 1,3-bis(hydroxymethyl)-5,5-dimethylhydantoin], which has the CAS Number 6440-58-0.

As used herein, "MDMH" or "MDM hydantoin" refers to 1-methylol-5,5-dimethylhydantoin,

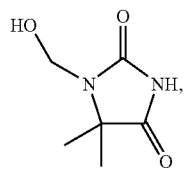

[i.e., 1-(hydroxymethyl)-5,5-dimethylhydantoin] which has the CAS number 116-25-6.

As used herein, "chitosan" refers to

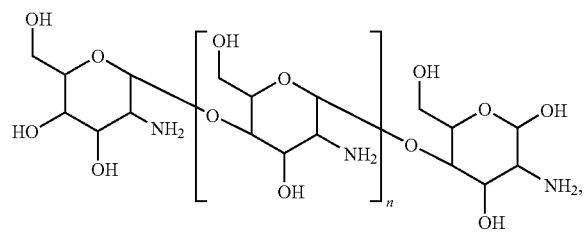

wherein n is about 3 to about 6000.

As used herein, "textile" refers to a material containing natural and/or artificial fibers. In some cases, the textile comprises about 5% to about 90% cellulose. The antimicrobial compositions of the present disclosure may be applied during or after processing to textiles such as clothing, including uniforms, socks, undergarments; medical textiles, including patent drapes, gauzes, surgeon's gowns, caps, and masks; and household textiles, including carpet, bedding, and drapes.

As used herein, "antimicrobial" or "antimicrobial composition" refers to a substance capable of killing or inhibiting the growth of microorganisms, such as bacteria (e.g., *Streptococcus, Enterococcus*, Bacteroidaceae, Enterobacteriaceae, Vibrionaceae, Pasteurellae, Pseudomonadaceae, *Escherichia coli, Staphylococcus aureus, Shigalla sonnei, Salmonella enteritidis, Salmonella choterse-suis, Pseudomonas aeruginosa*, VRE, MRSA, *Proteus mirabilis, Campylobacter jejuni*, and *Brevibacterium*), viruses (e.g., MS-2 Bacteriophage, Canduda albicans, influenza strain A, influenza strain B, and Swine Influenza), fungi (e.g., *Malassezia furfur* and *Trichophyton mentagrophytes*), and protozoans.

II. Embodiments of the Present Disclosure

Embodiments of the present disclosure include antimicrobial compositions, methods of preparing these antimicrobial compositions, and textiles including these compositions. Accordingly, embodiments of the present disclosure include textiles treated with the antimicrobial compositions described below and methods of applying these antimicrobial compositions to textiles. Examples of textiles which may be treated with the antimicrobial compositions described below include medical textiles, housing textiles, and textiles related to garments.

Embodiments of the antimicrobial compositions of the present disclosure may be added to a variety of textiles. Textiles that have been treated with the antimicrobial compositions or treated antimicrobial compositions of the present disclosure demonstrate antimicrobial activity. Moreover, the antimicrobial effect demonstrated by these treated textiles is highly durable, such that these textiles may be washed numerous times with little to no loss of antimicrobial activity. In certain embodiments, the antimicrobial aspect of the textile is renewable or regenerable without the addition of chlorine bleach. Additionally, textiles treated with the antimicrobial compositions of the present disclosure demonstrate negligible leaching and are thus unlikely to pose health concerns to those coming into contact with these treated textiles.

An embodiment of the present disclosure includes antimicrobial compositions in the form of an aqueous solution consisting of water, an organic acid present in about 0.1% to about 10% by weight of solution, chitosan present in about 0.1% to about 10% by weight of solution, as well as one or more heterocyclic N-halamine compounds present in about 5% to about 90% by weight of solution. Examples of organic acids suitable for use in the antimicrobial compositions of the present disclosure include, but are not limited to, citric acid, acetic acid, lactic acid, formic acid, and oxalic acid. Examples of heterocyclic N-halamine compounds suitable for use in the antimicrobial compositions of the present disclosure include, but are not limited to MDMH, DMDMH; monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, and 5,5-dimethylhydantoin; and monomethoxylated and dimethoxylated derivatives of monomethylolated and dimethylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, 5,5-dimethylhydantoin. Examples of the monomethoxylated and dimethoxylated compounds are monomethoxymethyl-5,5-dimethylhydantoin and 1,3-dimethoxymethyl-5,5-dimethylhydantoin, respectively.

One embodiment of the present disclosure includes an aqueous solution consisting of water, citric acid, chitosan, and DMDMH, e.g., an aqueous solution consisting of water, about 0.2% to about 1.0% of citric acid by weight of solution, about 0.2% to about 1.0% chitosan by weight of solution, and about 30% to about 35% DMDMH by weight of solution.

One embodiment of the present disclosure includes an aqueous solution consisting of water, citric acid, chitosan, and MDMH, e.g., an aqueous solution consisting of water, about 0.2% to about 1.0% of citric acid by weight of solution, about 0.2% to about 1.0% chitosan by weight of solution, and about 30% to about 35% MDMH by weight of solution.

One embodiment of the present disclosure includes an aqueous solution consisting of water, citric acid, chitosan, DMDMH, and MDMH, e.g., an aqueous solution consisting of water, about 0.2% to about 1.0% of citric acid by weight of solution, about 0.2% to about 1.0% chitosan by weight of solution, about 20% to about 25% DMDMH by weight of solution, and about 20% to about 25% MDMH by weight of solution.

In addition to the aforementioned embodiments, embodiments of the present disclosure may also include compositions comprising the antimicrobial compositions of the present disclosure. For example, embodiments of the present disclosure may include each of the ingredients of the antimicrobial compositions as described and further include additives used to ready the antimicrobial composition of the present disclosure for application to textiles. Examples of additives that may be used in conjunction with the antimicrobial compositions of the present disclosure include, but are not limited to, an ionic halide salt, an organic acid, and water. Examples of ionic halide salts suitable for use as treatment solutions for use in conjunction with the antimicrobial compositions of the present disclosure include, but are not limited to, magnesium chloride, magnesium bromide, calcium chloride, calcium bromide, potassium chloride, and combinations thereof.

One embodiment of the present disclosure includes an aqueous solution comprising water, an organic acid present in about 0.1% to about 10% by weight of solution, chitosan present in about 0.1% to about 10% by weight of solution, and one or more N-halamine compounds (e.g. MDMH and/or DMDMH) present in about 5% to about 90% by weight of solution. The solution can be diluted with water, pH adjusted to about 1.0 to about 5.0 using an organic acid (e.g., citric acid, acetic acid, and/or lactic acid), and can further comprise an ionic halide salt (e.g., magnesium chloride, magnesium bromide, and/or calcium chloride) present in about 1% to about 10% by weight of solution.

One embodiment of the present disclosure includes an aqueous solution comprising water, citric acid, chitosan, and DMDMH, e.g., an aqueous solution of water, about 0.2% to about 1.0% of citric acid by weight of solution, about 0.2% to about 1.0% chitosan by weight of solution, and about 30% to about 35% DMDMH by weight of solution. The solution can be diluted with water, pH adjusted to about 3.0 to about 3.5 using citric acid, and can further comprise magnesium chloride present in about 4.0% to about 7.0% by weight of solution.

One embodiment of the present disclosure includes an aqueous solution comprising water, citric acid, chitosan, and MDMH, e.g., an aqueous solution consisting of water, about 0.2% to about 1.0% of citric acid by weight of solution, about 0.2% to about 1.0% chitosan by weight of solution, and about 30% to about 35% MDMH by weight of solution. The solution can be diluted with water, pH adjusted to about 3.0 to about 3.5 using citric acid, and can further comprise magnesium chloride present in about 4.0% to about 7.0% by weight of solution.

One embodiment of the present disclosure includes an aqueous solution comprising water, citric acid, chitosan, DMDMH, and MDMH, e.g., an aqueous solution consisting of water, about 0.2% to about 1.0% of citric acid by weight of solution, about 0.2% to about 1.0% chitosan by weight of solution, about 20% to about 25% DMDMH by weight of solution, and about 20% to about 25% MDMH by weight of solution. The solution can be diluted with water, pH adjusted to about 3.0 to about 3.5 using citric acid, and can further comprise magnesium chloride present in about 4.0% to about 7.0% by weight of solution.

One embodiment of the present disclosure includes a method of treating textiles with the antimicrobial compositions of the present disclosure. The textiles can be treated by either applying the antimicrobial composition to the textile, or immersing the textile in the antimicrobial composition. For example, textiles may be sprayed with the antimicrobial compositions of the present disclosure. Alternatively, textiles may be dipped into baths of the antimicrobial compositions of the present disclosure. Regardless, treatment results in a textile composing an antimicrobial composition. Addition of the antimicrobial compositions of the present disclosure to such textiles results in the heterocyclic N-halamine compound covalently bonding to the cellulose:

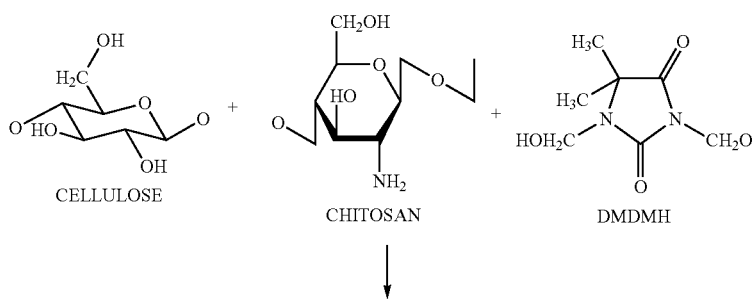

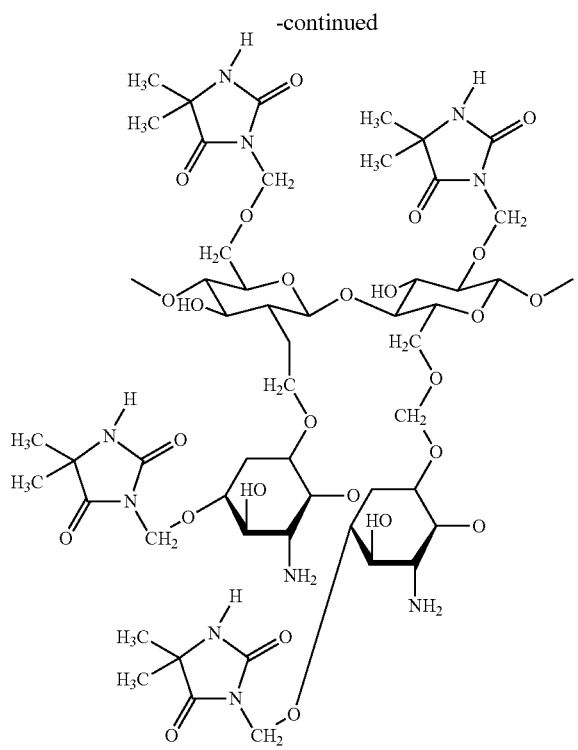

EXAMPLES

The following synthetic and biological examples are offered to illustrate embodiments of the present disclosure, and are not to be construed in any way as limiting the scope of the disclosure. In the examples below, abbreviations have their generally accepted meanings.

Example 1

10 g of chitosan,

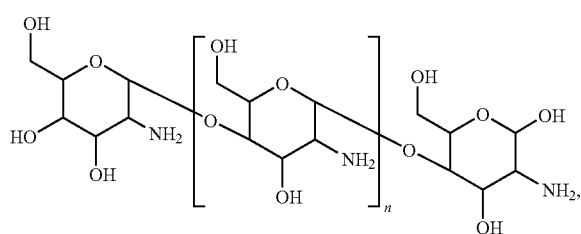

and 10 g of citric acid,

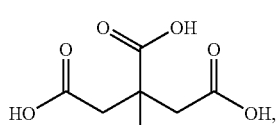

are dissolved in 980 g of $H_2O$. The resulting solution is combined with 1500 g of a solution containing 55% of DMDMH,

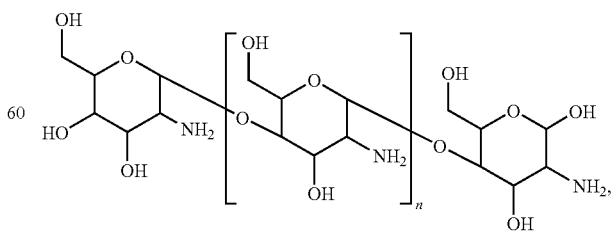

by weight of solution to produce approximately 2500 g of an antimicrobial composition which is approximately:

0.4% citric acid by weight of solution,
0.4% chitosan by weight of solution,
33% DMDMH by weight of solution, and
66.2% $H_2O$ by weight of solution.

Example 2

10 g of chitosan, and 10 g of citric acid,

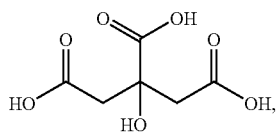

are dissolved in 980 g of H$_2$O. The resulting solution is combined with 1500 g of a solution containing 55% of MDMH,

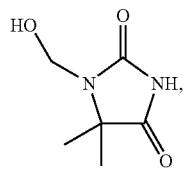

by weight of solution to produce approximately 2500 g of an antimicrobial composition which is approximately:
- 0.4% citric acid by weight of solution,
- 0.4% chitosan by weight of solution,
- 33% MDMH by weight of solution, and
- 66.2% H$_2$O by weight of solution.

Example 3

10 g of chitosan,

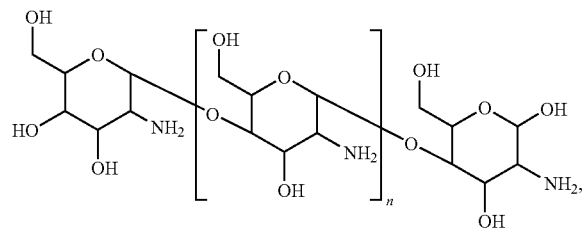

and 10 g of citric acid,

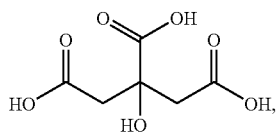

are dissolved in 780 g of H$_2$O. The resulting solution is combined with 1700 g of a solution containing 33.2% by weight DMDMH,

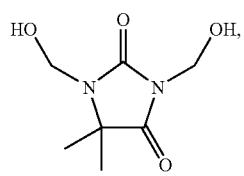

and 31.5% MDMH,

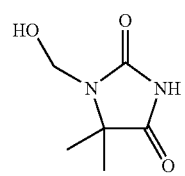

to produce an antimicrobial composition which is approximately:
- 0.4% citric acid by weight of solution,
- 0.4% chitosan by weight of solution,
- 22.6% DMDMH by weight of solution, and
- 21.4% MDMH by weight of solution.
- 55.2% H$_2$O by weight of solution.

Example 4

The composition of Example 1, made up of citric acid, chitosan, DMDMH, and water, may be put into a form convenient for textile treatment. Approximately 2500 g of an antimicrobial composition which is approximately:
- 0.4% citric acid by weight of solution,
- 0.4% chitosan by weight of solution,
- 33% DMDMH by weight of solution, and
- 66.2% H$_2$O by weight of solution is diluted by 39.16 kg H$_2$O forming a 41.66 kg dilute antimicrobial composition. pH of the resulting dilute antimicrobial composition is kept in the range of about 3.0 to about 3.5 using citric acid. Finally, 250 g of magnesium chloride is added to the solution to produce a treated antimicrobial composition for use in textile treatment.

Example 5

The composition of Example 2, made up of citric acid, chitosan, MDMH, and water, may be put into a form convenient for textile treatment. Approximately 2500 g of an antimicrobial composition which is:
- 0.4% citric acid by weight of solution,
- 0.4% chitosan by weight of solution,
- 33% MDMH by weight of solution, and
- 66.2% H$_2$O by weight of solution is diluted by 39.16 kg H$_2$O forming a 41.66 kg dilute antimicrobial composition. pH of the resulting dilute antimicrobial composition is kept in the range of about 3.0 to about 3.5 using citric acid. Finally, 250 g of magnesium chloride is added to the solution to produce a treated antimicrobial composition for use in textile treatment.

Example 6

The composition of Example 3, made up of citric acid, chitosan, DMDMH, MDMH, and water, may be put into a form convenient for textile treatment. Approximately 2500 g of an antimicrobial composition which is:
- 0.4% citric acid by weight of solution,
- 0.4% chitosan by weight of solution,
- 22.6% DMDMH by weight of solution, and
- 21.4% MDMH by weight of solution.
- 55.2% H$_2$O by weight of solution is diluted by 39.16 kg H$_2$O forming a 41.66 kg dilute antimicrobial composition. pH of the resulting dilute antimicrobial composition is kept in the range of about 3.0 to about 3.5 using citric acid. Finally, 250 g of magnesium chloride is added to the solution to produce a treated antimicrobial composition for use in textile treatment.

Example 7

10 g of chitosan,

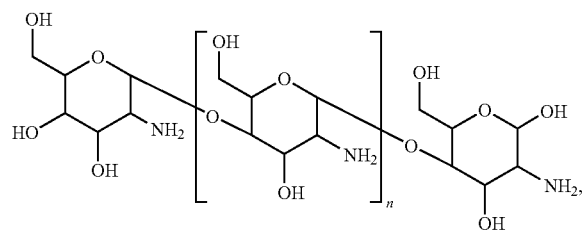

and 10 g of citric acid,

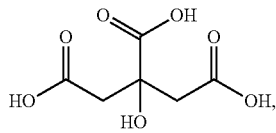

are dissolved in 480 g of H₂O. The resulting solution is combined with 2000 g of a solution containing 32% of DMDMH,

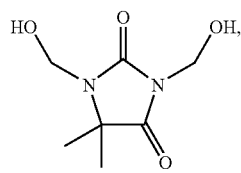

by weight of solution and 7.5% MDMH,

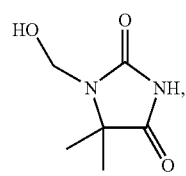

by weight of solution to produce approximately 2500 g of an antimicrobial composition which is:
- 0.4% citric acid by weight of solution,
- 0.4% chitosan by weight of solution,
- 25.6% DMDMH by weight of solution,
- 5.6% MDMH by weight of solution, and
- 68% H₂O by weight of solution.

We claim:
1. An aqueous solution consisting of:

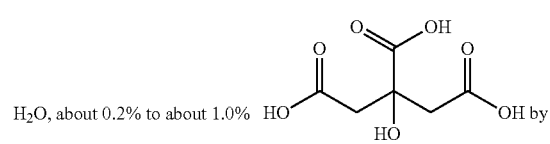

H₂O, about 0.2% to about 1.0% weight of solution,

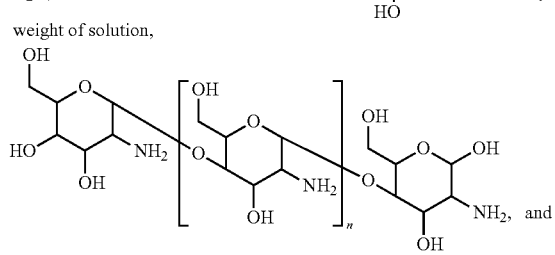

an additional compound selected from a group consisting of:

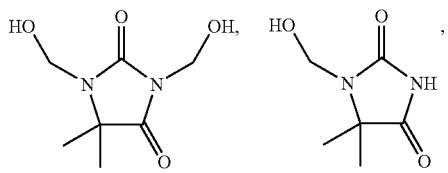

and a combination thereof,
wherein n is about 3 to about 6000.

2. The solution of claim 1, wherein the additional compound is

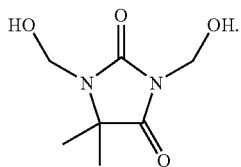

3. The solution of claim 1, wherein the additional compound is

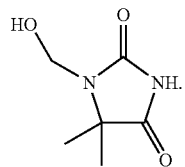

4. The solution of claim 1, wherein the additional compounds are the combination of

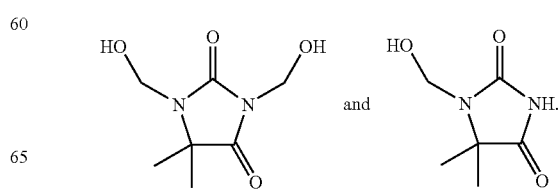

5. The solution of claim 2 consisting of:
H₂O, about 0.2% to about 1.0% of

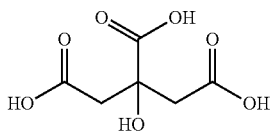

by weight of solution;
about 0.2% to about 1.0% of

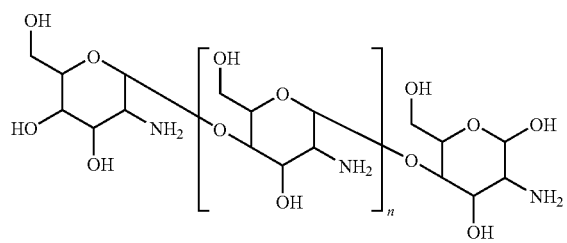

by weight of solution; and
about 30% to about 35% of

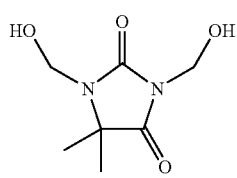

by weight of solution.

6. The solution of claim 3 consisting of:
H₂O, about 0.2% to about 1.0% of

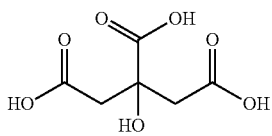

by weight of solution;
about 0.2% to about 1.0% of

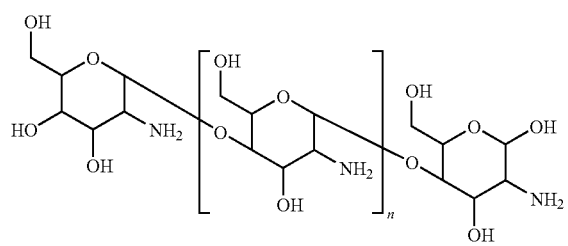

by weight of solution; and
about 30% to about 35% of

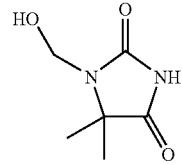

by weight of solution.

7. The solution of claim 4 consisting of:
H₂O, about 0.2% to about 1.0% of

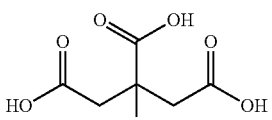

by weight of solution;
about 0.2% to about 1.0% of

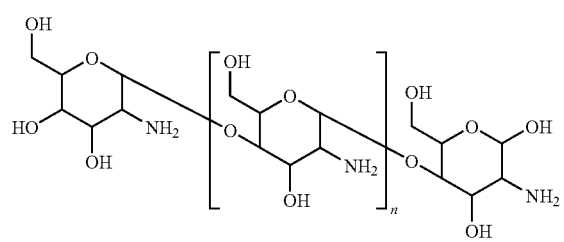

by weight of solution; and
about 20 to about 25% of

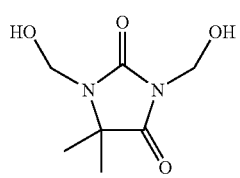

by weight of solution; and
about 20 to about 25% of

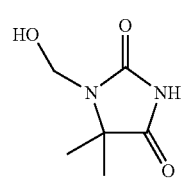

by weight of solution.

8. An aqueous solution comprising:

H₂O, about 0.2% to about 1.0% 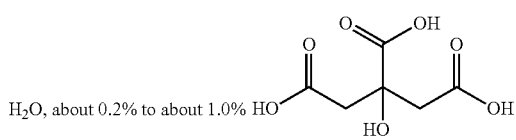 by weight of solution,

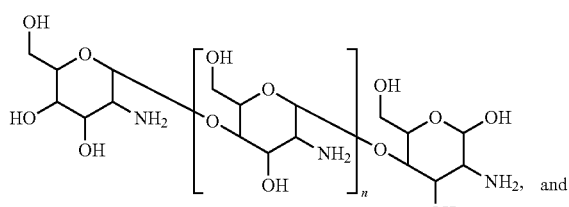

an additional compound selected from a group consisting of:

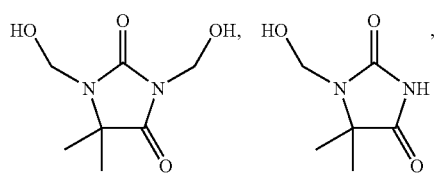

and a combination thereof, wherein n is about 3 to about 6000.

9. The aqueous solution of claim 8, further comprising MgCl₂.

10. The aqueous solution of claim 9, wherein

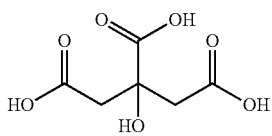

is present in about 0.2% to about 1.0% by weight of solution;

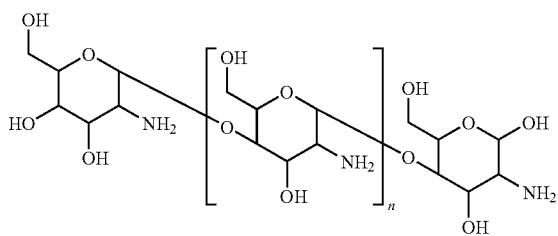

is present in about 0.2% to about 1.0% by weight of solution; and the additional compound is

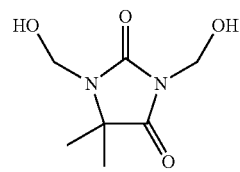

and is present in about 30% to about 35% by weight of solution.

11. The aqueous solution of claim 9, wherein

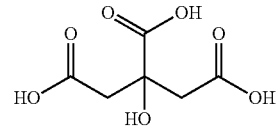

is present in about 0.2% to about 1.0% by weight of solution;

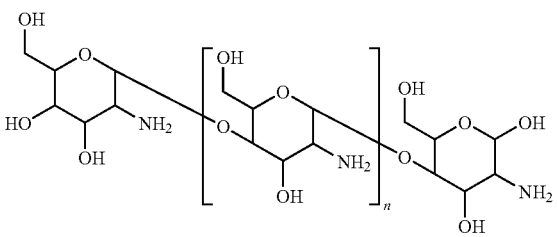

is present in about 0.2% to about 1.0% by weight of solution; and the additional compound is

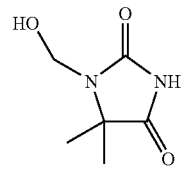

and is present in about 30% to about 35% by weight of solution.

12. The aqueous solution of claim 9, wherein

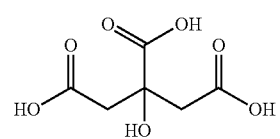

is present in about 0.2% to about 1.0% by weight of solution;

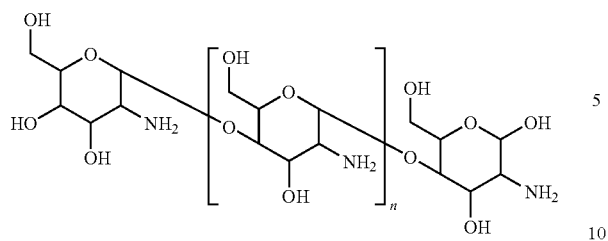

is present in about 0.2% to about 1.0% by weight of solution; and the additional compounds are

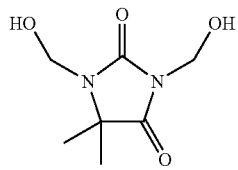

and is present in about 20% to about 25% by weight of solution and

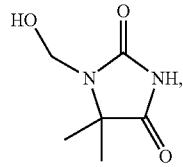

present in about 20% to about 25% by weight of solution.

13. A textile treated with the aqueous solution of claim 1.

14. A textile treated with the aqueous solution of claim 8.

15. A method of adding the aqueous solution of claim 1 to a textile, comprising contacting the textile with the aqueous solution of claim 1.

16. A method of adding the aqueous solution of claim 8 to a textile, comprising contacting the textile with the aqueous solution of claim 8.

* * * * *

UNITED STATES PATENT AND TRADEMARK OFFICE
CERTIFICATE OF CORRECTION

| | | |
|---|---|---|
| PATENT NO. | : 8,030,372 B2 | |
| APPLICATION NO. | : 12/553513 | |
| DATED | : October 4, 2011 | |
| INVENTOR(S) | : Rosing et al. | |

It is certified that error appears in the above-identified patent and that said Letters Patent is hereby corrected as shown below:

Title Page, Item (73) should read

--(73) Assignee: BioMed Protect, LLC
St. Louis, MO--

Signed and Sealed this
Thirtieth Day of October, 2012

David J. Kappos
*Director of the United States Patent and Trademark Office*